United States Patent [19]

Weichselbaum et al.

[11] 3,933,652

[45] Jan. 20, 1976

[54] PROCESS OF MANUFACTURING A POROUS, STAINLESS STEEL FILTER ELEMENT AND SEALING IT IN A TUBULAR FITTING, AND RESULTING FILTER

[75] Inventors: Theodore E. Weichselbaum, Normandy; William W. Gusky, Florissant, both of Mo.

[73] Assignee: Sherwood Medical Industries Inc., St. Louis, Mo.

[22] Filed: Apr. 25, 1973

[21] Appl. No.: 354,309

[52] U.S. Cl. .............. 210/446; 29/182.3; 29/191.2; 75/222; 210/451; 210/503; 210/510; 210/DIG. 23; 264/111; 264/125
[51] Int. Cl.[2] ... B01D 39/02; B22F 3/16; B22F 7/02
[58] Field of Search .......... 29/191.2, 192, 420, 182; 75/212, 222; 128/214 C, 221; 210/23, 446, 448, 451, 510, DIG. 23, 499, 503; 264/111, 125

[56] References Cited
UNITED STATES PATENTS

| | | | |
|---|---|---|---|
| 1,051,814 | 1/1913 | Lowendahl | 75/222 |
| 1,974,173 | 9/1934 | Calkins | 75/222 X |
| 2,239,800 | 4/1941 | Vogt et al. | 75/222 X |
| 2,297,817 | 10/1942 | Truxell, Jr. et al. | 210/510 X |
| 2,540,233 | 2/1951 | Beaver | 210/510 X |
| 2,554,343 | 5/1951 | Pall | 75/222 X |
| 2,857,913 | 10/1958 | Miskel | 128/221 |
| 2,864,366 | 12/1958 | Miskel | 128/221 |
| 2,902,363 | 9/1959 | Joyner | 75/222 X |
| 3,121,685 | 2/1964 | Hazell | 210/496 X |
| 3,539,472 | 11/1970 | Findeisen | 264/111 X |
| 3,722,697 | 3/1973 | Burke et al. | 128/214 C X |
| 3,788,486 | 1/1974 | Bergstrom | 210/510 X |
| 3,817,389 | 6/1974 | Weichselbaum | 210/448 |

OTHER PUBLICATIONS

"Stainless Steel", The Mining Magazine (London), Vol. 77, Oct. 1947, p. 207.
"Presses and Processes for Metal Powder Products", 4/17/44, The Electrochemical Society, pp. 137–160.

Primary Examiner—John Adee
Assistant Examiner—Robert H. Spitzer
Attorney, Agent, or Firm—Gardner and Anten

[57] ABSTRACT

An improved filter for medical infusion and injection equipment is manufactured by compacting stainless steel powder particles of an irregular or dendritic shape, in the substantial absence of a binder, to form a porous, self-supporting green article, and thereafter sintering the green article. The resulting filter is porous with the pores communicating with one another to form a network of tortuous or winding paths having lateral, oblique and vertical segments which function to trap contaminating particles of a solution passed therethrough. The porous filter is sealed in a tubular fitting by force-fitting the filter into the internal peripheral wall of an annular plastic bead in the fitting and heating the filter to cause the plastic bead to soften or melt and flow into the pores of the filter along a continuous peripheral ring.

22 Claims, 9 Drawing Figures

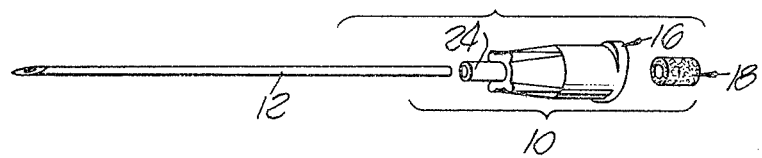
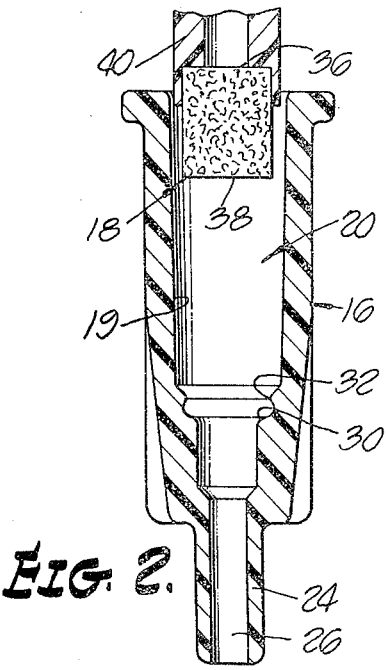
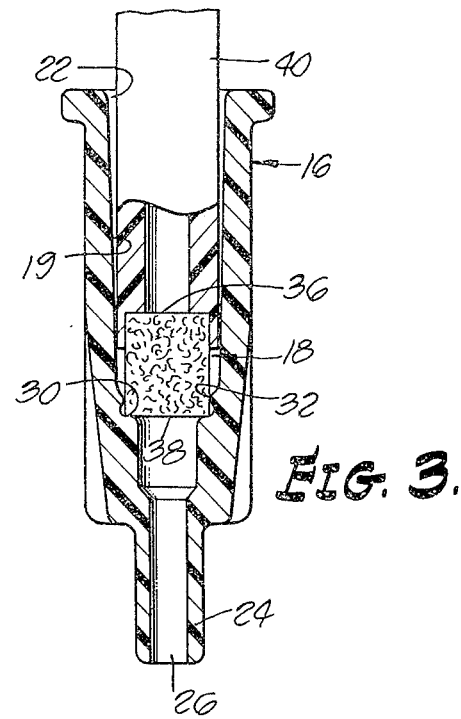
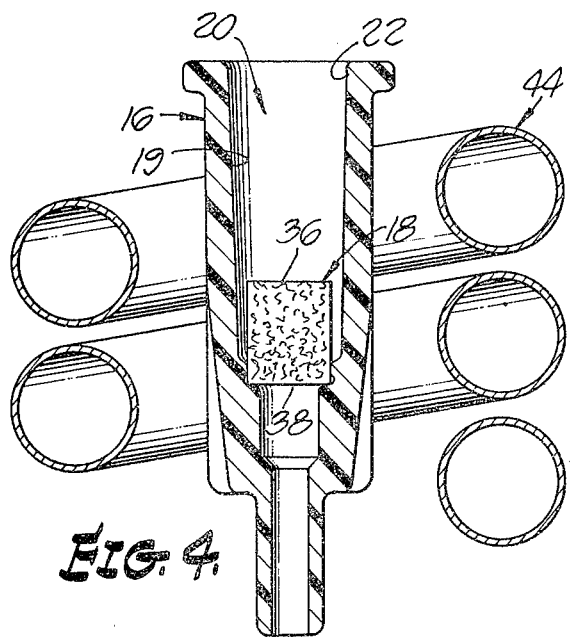
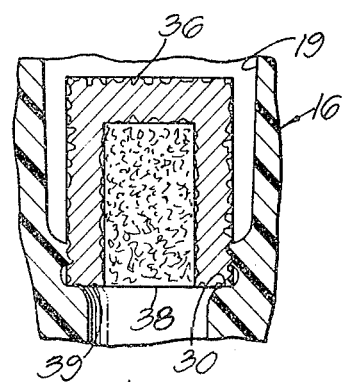

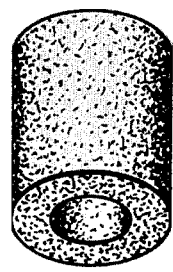
FIG. 6.
FIG. 7.
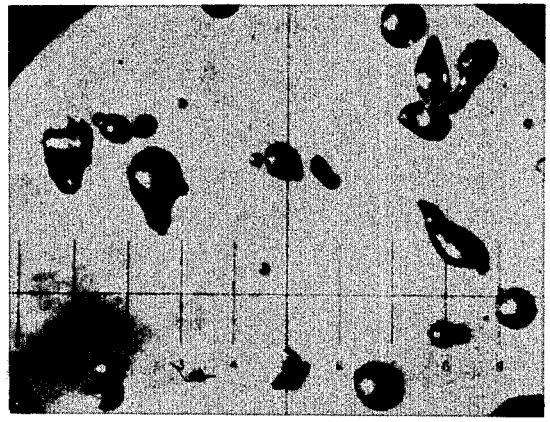
FIG. 8.
FIG. 9.

3,933,652

PROCESS OF MANUFACTURING A POROUS, STAINLESS STEEL FILTER ELEMENT AND SEALING IT IN A TUBULAR FITTING, AND RESULTING FILTER

BACKGROUND OF THE PRESENT INVENTION

The present invention relates generally to medical equipment and, more specifically, to filters and filter devices for use in medical injection and infusion equipment, such as hypodermic needles and intravenous infusion sets, and to methods of making such filters and filter devices.

In recent years medical researchers have been expressing increasing concern about the presence of particulate contamination in parenteral solutions intravascularly infused or injected into patients, and about the possible harm such contamination may cause. The term "parenteral solutions" as used throughout this patent is intended to refer to any solution intravenously or intramuscularly fed to a patient, including medication injected by a hypodermic syringe and various solutions (e.g., glucose, blood, medication, etc.) fed intravenously through an inravenous infusion set.

It is estimated that the average hospital patient currently receives approximately 2.5 liters of parenteral solutions during his illness, and the critically ill patient may receive as much as 100 liters or more. Recent studies have shown that the parenteral solutions are often comtaminated by particulate matter from the infusion equipment, e.g., the glass or plastic container for the solution, the tubing set, the stopper or "bung" and other accessories of the equipment. Obviously such contamination may be harmful to the patient, depending on the type, size, quantity, etc., of the contaminating particles. Harmful effects have been demonstrated by medical researchers by means of human autopsies and studies on various animals.

Particulate contamination is also present in the parenteral solutions injected into patients by means of hypodermic syringes. Sources of such contamination include the syringe barrels, plungers (which typically have rubber tips) and the covers (typically rubber) and interior (typically glass) of multi-dose vials from which solutions to be injected are withdrawn.

It is thus apparent that there is a need in the medical field for some means to prevent or minimize particulate matter contamination in parenteral solutions infused or injected into patients.

SUMMARY OF THE PRESENT INVENTION

It has been suggested that filters be employed in infusion and injection equipment to filter particulate contamination from the parenteral fluids fed to patients. However, there are numerous requirements and standards which any such filter must meet, and no filter or filter device heretofore designed has fully satisfied these requirements and standards or met with any appreciable acceptance or use in the medical field.

One of the requirements that any filter for medical injection or infusion equipment must meet is that it must pass the fluid to be injected or infused at a relatively high rate initially, and, in the case of infusion equipment, at a reasonably high rate over an extended period of time.

Another requirement of filters for medical infusion and injection equipment is that the filter be efficient in removing particulate contamination from the fluid to be infused or injected.

Still another requirement of filters for medical injection and infusion equipment is that the filters must provide a reasonably good measure of protection against air embolism; i.e., the filter must have the ability to prevent air bubbles from passing therethrough.

Yet another requirement of filters for medical injection and infusion equipment is that shedding of the filter in use must be minimal or non-existent to avoid introduction of foreign matter into the solution to be infused or injected.

Still another requirement of filters for medical infusion and injection equipment is that the filters be compatible with the various drugs or other solutions to be infused or injected; i.e., the filter material must not react with the infused or injected fluid to form matter which might be harmful to the patient.

Another requirement of filters for medical infusion and injection equipment is that the filter be compatible with the size, shape and material of the infusion or injection equipment, particularly the tubular member (e.g., the hub or other fitting) in which the filter is disposed, and, preferably, the filter should be compatible with existing standard infusion and injection equipment.

Another requirement is that the filter must be effectively sealed or bonded in he fluid flow line of the infusion or injection equipment to insure that the filter will perform its function effectively and efficiently, i.e., that no particulate contamination will leak between the filter and the interior wall of the fitting in which it is disposed.

A further requirement is that the filter and means of incorporation of the filter into the injection or infusion equipment must not add appreciably to the cost of the equipment, particularly in view of the fact that most of the injection and infusion equipment in use today is disposable (i.e., designed to be discarded after a single use).

In view of the foregoing, it is an object of the present invention to provide an improved filter and filter device for medical injection and infusion equipment which is highly efficient in removing particulate contamination from parenteral fluids to be infused or injected into patients while permitting relatively high flow rate of parenteral fluids therethrough.

It is a further object of the present invention to provide a filter and filter device for medical infusion and injection equipment which does not shed in use.

It is another object of the present invention to provide an improved filter and filter device for medical infusion and injection equipment which is compatible in size, shape and material, with the parenteral fluids to be filtered and with existing standard medical infusion and injection equipment.

It is a further object of the present invention to provide an improved filter and filter device for medical infusion and injection equipment which provides a relatively high degree of protection against air embolism.

It is a further object of the present invention to provide a filter device for medical infusion and injection equipment which is effectively and economically sealed or bonded in the fluid flow line of the equipment.

Another object of the present invention is to provide a filter and filter device for medical infusion and injection equipment which does not add appreciably to the cost of the equipment and, thus, is suitable and practical for use in disposable equipment.

The methods of manufacture of the present invention yield a filter and filter device which satisfy and realize the several objects discussed above. Essentially, the method of manufacturing the filter element of the present invention comprises the steps of compacting metal particles having an irregular or dendritic shape in a suitable mold to cause the projections or arms on the irregular peripheries of the dendritic particles to interlock with one another and produce a self-supporting green porous article, and thereafter sintering the green article. The resulting filter element comprises a plurality of pores communicating with one another along tortuous or winding paths having laterally extending portions, vertically extending portions and obliquely extending portions which trap or catch contaminating particles in solutions passed through the filter.

The filter element is force-fit into a plastic tubular member (e.g., a hub) and heated to soften or melt the adjacent internal peripheral wall of the tubular member which then flows into the pores of the filter to form a continuous peripheral seal between the filter and the tubular member.

Before proceeding to a detailed description of the preferred embodiments of this invention, it is to be noted that the permissible rate of flow of a solution through a filter and the efficiency of a filter ordinarily vary inversely with one another, i.e., the higher the permissible flow rate, the lower the efficiency, and the higher the efficiency, the lower the permissible flow rate. This is due to the fact that the permissible flow rate and the efficiency of a filter are largely governed by the size and pattern of the pores in the filter: the larger the pores, the higher the permissible flow rate and the lower the efficiency, and the smaller the pores, the lower the permissible flow rate and the higher the efficiency.

It is also to be noted that since a filter is employed for the very purpose of catching and retaining particles, any filter will become at least partially clogged through continued use to progressively increase the efficiency of the filter and decrease the permissible flow rate.

The factors governing the initial flow rate of a parenteral solution through a filter are:
a. The effective surface area of the filter exposed to the solution to be infused or injected.
b. The wall thickness of the filter through which the solution to be infused or injected must pass.
c. The mean pore diameter of the filter.
d. The porosity of the filter, i.e., the ratio of the volume of the openings or pores to the volume of solid material.
e. The height of the solution to be infused above the needle, in the case of infusion equipment.
f. The venous pressure of the patient.
g. The viscosity and specific gravity of the solution to be infused or injected.
h. Flow restrictions in series with the filter, such as flow clamps in the intravenous infusion set, the drip orifice from the bottle of solution to be infused, the needle, the inside diameter of the tubing of the infusion set, etc.

The factors governing the long term flow rate include all of the foregoing factors, and further include the following factors:
a. Reduction in the level of the solution being infused, due to depletion.
b. The level of particulate contamination in the solution being infused or injected.
c. The pore structure of the filter (i.e., the pattern or arrangement of the pores in the filter).

The factors governing filter efficiency are:
a. The mean pore diameter of the filter.
b. The maximum pore diameter of the filter.
c. The number of pore minima connected in series, from filter input surface to filter output surface.
d. The integrity of the seal or bond of the filter to the filter housing (e.g., the hub).
e. The number of particles trapped in or on the filter from solution previously passed therethrough.
f. The distribution of size of the particles in the solution being filtered.
g. The particle density of the solution being filtered, i.e., the number of particles per volume of solution.
h. The stability of the shapes of particles in the solution.
i. The ratios of length to width to height of the particles in the solution.

Mean pore diameter and maximum pore diameter [factors (a) and (b) above] attempt to define, in a practical fashion, the distribution of pore sizes in the filter.

The most effective way to measure the efficiency of a filter is to put the filter to the task of fulfilling its function, e.g., to filter a particulate suspension and examine the filtrate for particles passed. The ratio of particles retained by the filter to particles passed therethrough in each size category (i.e., particle size) represents the efficiency of the filter for particles of that particular size. Thus, efficiency may be determined by the following equation:

$E = 100 (1-F/D)$, where
$E =$ filter efficiency in percent;
$F =$ particles per unit volume in the filtrate; and
$D =$ particles per unit volume in the particle suspension.

The filter of the present invention optimizes both the efficiency and permissible flow rate characteristics to permit maximum desired flow for the required efficiency. Among the features, which contribute to optimization of these important characteristics are the following:
a. The surface area of the filter is as large as possible, consistent with other parameters, such as size and cost requirements.
b. The wall thicknesses of the filter are as thin as possible, consistent with structural strength, manufacturing practicality and efficiency requirements.
c. The minimum pore diameter of the filter is as large as possible consistent with efficiency requirements (e.g., the size and quantity of particulate contamination which must be removed from the solution).
d. The porosity of the filter is as high as possible, consistent with practical considerations in manufacturing.
e. The pore structure or pattern of the filter is designed to resist "blinding" or blocking of the filter by entrapped particles.

Other objects, features and advantages of the present invention will be apparent from the following detailed description of preferred embodiments of the invention and the accompanying drawings.

BRIEF DESCRIPTION OF THE DRAWINGS

FIG. 1 is an exploded perspective view of a hypodermic needle into which a filter of the present invention may be incorporated.

FIG. 2 is a sectional elevation view of the hub or tubular fitting of the apparatus shown in FIG. 1 with a filter of the present invention being inserted therein.

FIG. 3 is a sectional elevation view similar to FIG. 2 showing the filter in place in the fitting.

FIG. 4 is a sectional elevation view similar to FIGS. 2 and 3 showing the filter being induction heated to seal it in the fitting.

FIG. 5 is a partial sectional elevation view showing in greater detail the seal between the filter and the fitting.

FIG. 6 is an enlarged perspective view of the filter shown in FIGS. 1-5.

FIG. 7 is a photomicrograph of some irregular or dendritic stainless steel particles from which the filter shown in FIG. 6 may be made.

FIGS. 8 and 9 are photomicrographs of portions of the surfaces of filters manufactured according to the teachings of the present invention, the surface areas having been magnified 100 times.

DETAILED DESCRIPTION OF THE PREFERRED EMBODIMENTS

FIG. 1 illustrates a hypodermic needle 10 into which the filter device of the present invention may be incorporated. The needle 10 includes a needle cannula 12 (preferably stainless steel) connected to the forward or distal end of a thermoplastic tubular hub or fitting 16 having a porous, sintered, powdered stainless steel filter 18 therein. The filter element 18 is manufactured according to the teachings of the present invention, described below. It is manufactured from stainless steel particles having an irregular or dendritic shape.

The hypodermic needle 10 of FIG. 1 is only an exemplary showing of a medical injection device into which the filter device of the present invention may be incorporated. It is contemplated that the filter device of the present invention may be incorporated in various types of medical equipment and the like, including intravenous infusion sets, hypodermic syringes and double luer adapters. The tubular thermoplastic fitting or connector 16 is exemplary of only one of numerous types of connectors, fittings, adapters and hubs into which a filter may be incorporated and sealed to form the filter device of the present invention.

As best shown in FIG. 6, the filter 18 illustrated herein is preferably cylindrical cup-shape in form, having a closed rear end 36 and an open forward end 38.

The cylindrical cup-shape of the filter element 18 maximizes the effective surface area of the filter which is exposed to the solution to be passed therethrough, consistent with the overall size limitations imposed by the fitting into which the filter is inserted, to maximize the permissible flow rate of the solution. For example, in the present invention filters having a surface area of about 0.06 sq. in. and a wall thickness of about 0.02 in. to 0.06 in. (preferably about 0.03 in.) are preferable. It is to be understood, however, that filters of various other shapes may be manufactured according to the present invention, such as disc shapes and plate shapes, for example.

According to a preferred embodiment of the present invention, the filter 18 is manufactured according to the following process:

1. Metal powder having particles of an irregular or dendritic shape are screened to obtain particles of the desired size.
2. A predetermined amount of the screened powder is blended with a predetermined, relatively small quantity of a lubricant.
3. The powder-lubricant blend is loaded into a suitable mold and compacted therein under a predetermined compaction pressure to obtain a self-supporting "green" filter.
4. The "green" filter is removed from the mold and subjected to a two step heating process to first "burn-off" the lubricant and thereafter sinter the filter.

The specific details associated with the foregoing basic steps, including times, temperatures, compaction pressure, materials, etc., will now be described.

Examples of stainless steel particles of irregular or dendritic shape are shown in the photomicrograph of FIG. 7. Stainless steel powder comprising particles such as those shown in FIG. 7 are screened to obtain stainless steel particles of the desired size. The size of the particles, along with other parameters, including the compaction pressure applied to the powder, will determine the efficiency of the filter and the permissible rate of flow of solution passed through the filter.

Two grades of filters are described herein. One grade is termed S3-5, and the second grade is termed S8-10. The filter grade identification indicates the efficiency of the filter. The S3-5 filter is designed to remove from the solution to be filtered 99% of all particles larger than five micrometers and 95% of all particles larger than three micrometers. The S8-10 filter is designed to remove 99% of all particles larger than ten micrometers and 95% of all particles larger than eight micrometers. As described below, these filter efficiencies have been achieved while permitting a relatively high rate of flow of solution through the filters.

The stainless steel powder from which the S3-5 filter has been manufactured have mean diameter particle sizes of between about 44 micrometers and 74 micrometers, also identified as having sieve cuts of 200/325 mesh.

The S8-10 filter has been manufactured from stainless steel powder whose mean diameter particle sizes are between about 125 and 149 micrometers, having sieve cuts of 100/120 mesh.

In both cases, the shapes of the particles are sufficiently irregular so that the "branches" or "arms" of adjacent particles lock together when the powder is compacted to form a self-supporting article.

The screening step employed may be the two step screening process wherein a larger mesh screen is first used to eliminate powder particles larger than the largest particle size desired (e.g., 74 micrometers for the S3-5 filter, 149 micrometers for the S8-10 filter) and a smaller mesh screen is then used to eliminate powder particles smaller than the smallest particle size desired (e.g., 44 micrometers for the S3-5 filter, 125 micrometers for the S8-10 filter).

Following the screening step, the stainless steel particles are mixed with a suitable lubricant and loaded into a suitable mold (e.g., a mold having a cup-shape) and compacted into the desired shape.

Any numbr of lubricants may be employed, such as a synthetic wax of general fatty acid origin, for example. One such wax is known as Acrawax C and is manufactured by the Glyco Chemical Co. of Greenwich, Connecticut.

The amount of lubricant should preferable be about 0.05% by weight of the green article, or greater, and may be as much as 0.5% by weight. It will be appreciated that the greater the amount of lubricant added, the longer the tool life of the mold and compacting equipment. The lubricant may be mixed with the stainless steel powder by tumbling the powder and lubricant in a suitable roller mill, for example.

The amount, by weight, of stainless steel powder to be mixed with the lubricant and loaded in the mold of the press equipment may be calculated in the following manner:

a. The volume of stainless steel powder in the cup-shaped filter $= TT/4[D^2 L-(D-2T)^2 (L-C)]$, where
  $D$ = the outside diameter of the filter;
  $L$ = the length of the filter;
  $TT$ = the constant, pi;
  $T$ = the wall thickness of the filter;
and
  $C$ = the thickness of the end wall of the filter.

b. The density of the stainless steel used, No. 316, equals 0.29 pounds per cubic inch, or 131.5418 grams per cubic inch.

c. During the subsequent sintering operation, the green filter may be expected to shrink approximately 0.0005 inches in diameter and approximately 1% in length.

d. The density of the compacted filter, after sintering = 1-P, where P = the desired porosity of the compacted, sintered filter.

e. $W_d = (131.542\ TT/4)\ (1\text{-}P)\ (1+S)\ [0.99L(D-.0005)^2 -(D-0.0005-2T)^2 0.99(L-C)]$ or $W_d = 102.2798(1\text{-}P)\ (1+S)\ [L(D-0.0005)^2 -(D-0.0005-2T)^2(L-C)]$ where
  $W_d$ = the desired weight, in grams, of the green filter;
  $p$ = the desired porosity of the sintered filter, expressed as a decimal fraction;
  $S$ = the weight of lubricant added to the stainless steel powder, expressed as a decimal fraction of powder weight;
  $L$ = the overall length, in inches, of the green filter;
  $D$ = the outside diameter, in inches, of the green filter;
  $TT$ = the constant, pi;
  $T$ = the cylindrical wall thickness, in inches, of the green filter; and
  $C$ = the thickness of the end wall of the green filter, in inches.

By way of example, if the green filter (the filter formed by compacting the powder and lubricant mix, prior to sintering) has the following approximate dimensions:

$D = 0.1280$ inch, $L = 0.1515$ inch, $C = 0.0303$ inch, $T = 0.030$ inch,
$P = 0.30$, $S = 0.0005$, and $W_d + 0.13685$ grams, after sintering the filter will have the following approximate dimensions:

$D = 0.1275$ inch, $L = 0.150$ inch, $C = 0.030$ inch, $T = 0.030$ inch,
$P = 0.30$, $S = 0.0000$, and $W_d + 0.136782$ grams.

The optimum pressure of compaction of the stainless steel powder-lubricant blend may be calculated according to the following formula:

$P_c = F_R/A_F$, where
  $P_c$ = the compaction pressure required to achieve the desired density of the pressed green filter;
  $F_R$ = the powder press ram force, in pounds, which may be measured indirectly by measurement of treadle deflection; and
  $A_F$ = the calculated area, e.g., $TTr^2$ of the end wall of the filter.

For example, $P_c = F_R/A_F = F_R/TTr^2 = 1600$ pounds$/.012767657$ sq. in. $= 62.7$ tons per sq. inch, where the ram force is 1600 pounds and the area of the end wall of the filter is .012767657 sq. in.

For the specific examples given, it has been discovered that; for the S3-5 filter, a filter density of about 5.6 gm/cm$^3$ will result in a desired porosity of 30.2% by pressing approximately 139 mg of powder and lubricant, while, for the S8-10 filter, a density of about 5.4 gm/cm$^3$ will result in a desired porosity of 33.0% by pressing approximately 133 mg of powder and lubricant.

After it has been determined that an acceptable filter can be manufactured using a given compaction pressure, the pressure figure can be used to make additional parts or parts of different sizes and shapes.

It has been found that the green filter made according to the foregoing steps and formulas are completely self-supporting and will not crumble when handled.

The green filter is then heated to a suitable temperature (e.g., between about 800°F and 1000°F for from 30 minutes to 90 minutes) to burn off the lubricant and, thereafter, is sintered at an increased temperature (e.g., between about 2000°F and 2400°F) for a suitable period (e.g., 15 to 90 minutes) to form the finished, sintered filter. Sintering is accomplished in a dry $H_2$ atmosphere.

It should be noted that there are a great many variable factors in manufacturing filters according to the present invention which will affect the characteristics of the finished filters and their performance in use. Tables A, B and C below set forth these variables which have been taken into consideration in arriving at many of the manufacturing parameters (e.g., times, temperatures, pressures, materials, etc.) described herein. Most of these variables are set forth in a book entitled "Fundamental Principles of Powder Metallurgy" by W. D. Jones, St. Martin's Press.

Table A sets forth those variables which have been shown to exert the greatest influence over the completed filter. Many of them show up in the mathematical equations set forth herein and are manipulated by the process of the present invention.

Table B includes variables, some of which may be manipulated, but with less frequency than the variables of Table A. Some of these variables, such as tool wear, are not manipulated, but are monitored.

Table C includes other variables, some of which are of subtle, or even questionable significance. Some of these variables are automatically manipulated when related variables in Tables A or B are manipulated.

Table A — Primary Control Variables 1. metal powder
   a. chemical composition and solid density
   b. particle size distribution
2. lubricant
   a. amount
3. press tooling
   a. cavity diameter
   b. filter end wall thickness adjustment
   c. filter end wall fill adjustment
4. presses a. fill adjustment, overall filter
b. compacted part height adjustment, overall filter
5. sintering
   a. chemical composition of metal powder
   b. temperature
   c. time Table B — Secondary Control Variables 1. metal powder
   a. flowability
   b. particle shape
2. lubricant
   a. chemical make-up
   b. particle size
   c. particle shape
   d. method of mixing
   e. completeness of mixing
3. press tooling
   a. wear
   b. tolerances
4. presses
   a. pressure variations
   b. speed
   c. vibration
   d. wear
   e. temperature rise
5. sintering
   a. rate of heating
   b. rate of cooling
   c. nature of atmosphere
   d. impurities in atmosphere
   e. rate of flow of atmosphere Table C — Tertiary Variables 1. metal powder
   a. apparent density
   b. compressibility
   c. ability to work harden
   d. absorbed gases
   e. segregation of constituents
2. lubricant
   a. temperature rise in mixing
   b. changes in storage after mixing, before pressing
3. press tooling
   a. materials
   b. stiffness
   c. clearances
   d. finish
4. presses
   a. alignment
   b. ejection stresses
   c. design
   d. method of filling
5. sintering
   a. activity of powder
   b. gas content of compacts
   c. amount and nature of lubricant
   d. thermal expansion of metals involved As noted above, many of the parameter values indicated in conjunction with the manufacturing process described above were determined according to the variables set forth in Tables A, B and C. Table D below sets forth the preferred parameter values which have been established for the S3-5 and S8-10 filters. Some of the values in Table D are called out specifically and others are described generally.

Table D

| | | Values of Parameters | |
|---|---|---|---|
| 1. | metal powder | S3–5 | S8–10 |
| | (a) particle size distribution - | 44–74 micrometer mean diameter (325/200 sieve mesh). | 125–149 micrometer mean diameter (120/100 sieve mesh). |
| | (b) particle shape - | must be of sufficiently irregular shape to hold together when compacted (green strength). | |
| | (c) flowability - | selected to optimize press speed. | |
| | (d) chemical composition - | Type 316 Stainless Steel | |
| | (e) particle solid density - | 8.03 gm/cm³ (0.29 lb/in³) | |
| 2. | lubricant | | |
| | (a) chemical composition - | synthetic wax of general fatty acid origin, such as Acrawax C. | |
| | (b) amount - | 0.05% by weight shown to be satisfactory, but up to 0.5% probably acceptable, with increased tool life an advantage. | |
| | (c) mixing - | tumbling in roller mill for about 25 minutes. | |
| | (d) particle size and shape - | atomized for good flow and easy mixing. | |
| 3. | pressing | | |
| | (a) amount (metal powder plus lubricant) - | 139 mg to achieve filter density of about 5.6 gm/cm³ (30.2% porosity) | 133 mg to achieve filter density of about 5.4 gm/cm³ (33.0% porosity) |
| 4. | sintering | | |
| | (a) lubricant burn-off time and temperature | 800°F to 1000°F (prefer about 850°F) for from 30–90 minutes (prefer about 60 minutes). | |
| | (b) sintering time and temperature | 2000°F to 2400°F (prefer about 2200°F) for from 15–90 minutes (prefer about 30 minutes). | |

The filter element resulting from the process described above is depicted in FIG. 6 of the drawings.

FIG. 7 of the drawings shows the dendritic or irregular shape of the stainless steel particles which are compacted, in the manner set forth above, to form the filter element. It will be noted that the dendritic particles have projections or branches or arms extending therefrom. These projections define the irregular particle shapes and, when compacted in the manner set forth above, interlock with one another to form a substantially self-supporting green filter element which can be handled without significant shedding or crumbling, before the lubricant "burn-off" and sintering steps. It is to be noted that the self-supporting nature of the green article formed by compacting the particles in the substantial absence of a binder is one of the several significant advantages of the filter and process of the present invention.

FIG. 8 of the drawings is a photomicrograph of a portion of the surface of an S3-5 filter manufactured according to the present invention and magnified one hundred times. FIG. 9 is a photomicrograph of a portion of the surface of an S8-10 filter manufactured according to the present invention and magnified one hundred times.

The pattern or arrangement of the internal pore structure of the filter element 18 is also illustrated by the photomicrographs of FIGS. 8 and 9. It may be seen from FIGS. 8 and 9 that the compacted dendritic particles define communicating pores therebetween. These communicating pores define a plurality of tortuous or winding pore paths having lateral, oblique and vertical components or sections. This arrangement of tortuous pore paths provides increased efficiency or particle catching ability of the filter. Particles which may pass through one, two, or more of the pores because of the size or disposition (e.g., lengthwise or end-on) of the particle will later be passed to a subsequent, perhaps smaller, pore in a different position (e.g., sideways) and will be trapped thereby.

Another way of defining the internal pore structure of the filter utilizes the terminology "pore minima". A pore minimum, as used herein, refers to the irregular plane figure defined by the intersection of a plane normal to the pore fluid flow with the particles which bound the pore, where the plane is located along the flow path at a point where the area of the plane figure is less than at adjacent points either ahead or behind on the flow path. Thus, the pore minimum defines the smallest particle which a given pore may trap. The pore structure of the filter of the present invention may be defined as comprising a series of multiple pore minima relieved by larger pores or pore portions. Since the pores are of different sizes and angular dispositions, a particle may pass through one or more pores, but will eventually be trapped by a pore having a pore minimum smaller than the particle.

Numerous tests and experiments confirm the high efficiency or particle catching ability of the filter of the present invention, and further confirm the ability of the filter to permit parenteral fluids to flow therethrough at a maximum rate for a given efficiency.

It has also been determined through numerous tests and experiments that the filters of the present invention offer a high measure of protection against air embolism, are completely compatible with drugs commonly injected or infused into human beings, and do not shed in use.

The method by which a filter 18 manufactured according to the present invention may be sealed in a tubular thermoplastic connector 16 and the resulting filter assembly or device may best be understood by referring to FIGS. 2 to 5.

The thermoplastic connector 16 is of generally tubular shape and has internal peripheral wall 19 defining a longitudinal passage 20 extending therethrough. The outer or proximal end 22 of the passage 20 is tapered outwardly (commonly referred to in the medical field as a female luer taper) to facilitate sealing reception of the tip of a syringe (or other tubular member) to which the proximal end of the fitting 16 is to be connected. The forward or distal end of the passage through the stem 24 may be cylindrical or tapered to receive the butt end of the needle cannula 12, which may, for example, be epoxy bonded therein.

The intermediate portion of the peripheral wall 19 of passage 20 is provided with a shoulder 30 which functions as a seat for the end of the filter 18. An inwardly-projecting annular ring or bead 32 is provided on the interior wall 19 of the fitting 16 just above the shoulder or seat 30. The internal diameter of the bead 32 is slightly less than the outer diameter of the filter 18 so that the end of the filter 18 can be forcefitted into the bead 32 in a manner and for a purpose described more fully below.

The term "thermoplastic", as used herein, is intended to refer to any plastic material that will soften when heated and re-solidify or harden when cooled. The thermoplastic fitting or connector 16 is preferably constructed of a relatively rigid thermoplastic such as polypropylene, polycarbonate or polyethylene terephthalate.

The filter 18 is preferably cylindrical cup-shaped in form, having a closed rear end 36 and an open forward end 38 defined by a forward peripheral wall 39.

The filter element 18 is positioned and sealed or bonded in the tubular fitting 16 in the following manner.

The filter element 18 is inserted, open end first, into the passage 20 of the fitting 16 by means of a suitable tool, such as the insertion tip 40 of a suitable vacuum tool, as shown in FIG. 2. The filter element 18 is held on the tool 40 by suction, and is pressed downwardly through the plastic annular ring or bead 32 until the forward peripheral wall 39 of the open forward end 38 rests or seats on the annular shoulder 30. As noted above, the outer diameter of the filter element 18 is slightly larger than the internal diameter of the annular bead 32 so that the forward end of the filter 18 is forcefitted in the annular bead 32 to compress and deform the bead (see FIG. 3).

With the filter element 18 in place (i.e., with the forward end wall 39 of the filter abutting the shoulder 30 in the fitting 16 and the forward end portion of the peripheral wall of the filter 18 force-fitted in the annular bead 32), the filter element 18 is heated to a temperature and for such a time to heat the thermoplastic bead 32, which melts or softens and flows into the pores in a continuous ring around the forward end portion of the outer peripheral wall of the filter element 18. As shown in FIG. 4, it is contemplated that the filter element 18 may be heated by the electromagnetic field generated by induction heating coils 44. It is contemplated, however, that other means of heating the filter element 18 may be employed so long as such heating means does not interfere with the compressive force exerted by the filter element on the annular bead 32.

FIG. 5 is an enlarged sectional view illustrating the intrusion of the plastic bead 32 into the pores around the outer peripheral wall of the forward end portion of the filter element 18 after the bead has cooled and re-solidified.

It is to be noted that the seal or bond formed between the bead 32 and the forward end portion of the outer surface of filter element 18 is a relatively thin continuous ring which does not significantly reduce the effective surface area of the filter which is exposed to the solution to be filtered. Thus, the seal will not inhibit the flow rate of the solutions which pass through the filter. It is to be noted that the foregoing is a significant advantage of the present invention because it is essential to maintain the effective surface area of the filter element 18 at a maximum to insure that the flow rate of the solution passed through the filter may be maintained at the desired level. It will also be noted that the cylindrical cup shape of the filter element 18 maximizes the effective surface area of the filter which is exposed to the solution to be passed therethrough, consistent with the over-all size limitations imposed by the fitting into which it is inserted, to maximize the permissible flow rate of the solution. The foregoing description of the overall configuration of the filter and method of bonding it within a tubular fitting or hub is more specifically described in the copending application of T. E. Weichselbaum for Method of Sealing Filter in Tubular Fitting for Medical Injection Equipment and The Like, and Resulting Filter Device, filed Jan. 15, 1973, Ser. No. 323,726, now U.S. Pat. No. 3,817,389 and assigned to the same assignee as the present invention.

From the foregoing, it will be appreciated that the method of the present invention provides a filter device for medical injection equipment and the like which is relatively inexpensive, efficient and readily adaptable for use with existing injection and infusion equipment (e.g., plastic fittings, such as injection needle hubs). The ring seal or bond formed between the tubular fitting and the peripheral wall of the filter provides an effective continuous seal which does not interfere with the critical, permissible flow rate of solution through the filter, yet insures a fluid tight seal to prevent fluid from passing around, rather than through, the filter element. Thus, the method and resulting filter device of the present invention satisfies the existing need in the industry for a device which will effectively eliminate or minimize particulate contamination in parenteral fluids to be injected into patients.

It is contemplated, of course, that numerous changes and modifications may be made to the particular embodiments of the method and filter device described above and shown in the drawings without departing from the scope of the present invention. For example, while a cylindrical cup-shaped filter has been shown and described as a preferrable embodiment, it is contemplated that method and filter devices of the present invention may employ filter elements of other shapes, such as disk shapes, plate shapes and rounded cup shapes.

Accordingly, it is intended that the scope of the present invention be limited only by the scope of the appended claims.

We claim:

1. A process for manufacturing a sintered, porous stainless steel filter for use in medical injection and infusion equipment and the like; said filter being manufactured from stainless steel particles having an irregular or dendritic shape with arm-like projections extending outwardly therefrom; said process comprising the steps of:
    screening dendritic stainless steel particles to obtain particles of a predetermined size;
    mixing the screened particles with a lubricant;
    loading the particle-lubricant mixture into a mold of desired shape;
    compacting the particle-lubricant mixture in the mold at a predetermined compaction pressure to cause the arm-like projections on the particles to engage and interlock with one another and form a self-supporting, porous, green filter;
    heating the green filter at a predetermined temperature to burn off the lubricant; and
    sintering the filter to form a sintered, porous, stainless steel filter.

2. A process of manufacturing a filter according to claim 1, wherein said screening step comprises screening stainless steel particles to obtain particles having mean diameters of between about 44 and 74 micrometers.

3. A process of manufacturing a filter according to claim 2, wherein the mixture is compacted to a density of about 5.6 gm/cm$^3$.

4. The product of the process of claim 3.

5. The product of the process of claim 2.

6. A process of manufacturing a filter according to claim 1, wherein said screening step comprises screening stainless steel particles to obtain particles having mean diameters of between about 125 and 149 micrometers.

7. A process of manufacturing a filter according to claim 6, wherein the mixture is compacted to a density of about 5.4 gm/cm$^3$.

8. The product of the process of claim 7.

9. The product of the process of claim 6.

10. A process of manufacturing a filter according to claim 1, wherein said step of mixing the screened particles with a lubricant comprises mixing the screened particles with a synthetic wax of general fatty acid origin.

11. The product of the process of claim 10.

12. A process of manufacturing a filter according to claim 1, wherein said step of sintering said filter comprises heating said filter at a temperature of between about 2000°F, and about 2400°F, for about 30 minutes.

13. The product of the process of claim 12.

14. The product of the process of claim 1.

15. A process for manufacturing a porous filter fir use in medical injection and infusion equipment and the like, said filter being manufactured from metal particles having an irregular or dendritic shape with arm-like projections extending outwardly therefrom; said process comprising the steps of:
    screening dendritic metal particles to obtain dendritic particles of a predetermined size;
    mixing the screened dendritic particles with a lubricant;
    loading the particle-lubricant mixture into a mold;
    compacting the particle-lubricant mixture in the mold at a predetermined compaction pressure to cause the arm-like projections on the particles to engage and interlock with one another and form a self-supporting green article;
    heating the green article at a predetermined temperature to burn off the lubricant; and
    sintering the filter to form a sintered, porous metal filter.

16. The product of the process of claim 15.

17. A process for making a filter device of metal particles for medical injection and infusion equipment and the like, said filter of said filter device being manufactured from metal particles having an irregular or dendritic shape with arm-like projections extending outwardly therefrom; said process comprising the steps of:
    screening the metal particles to obtain particles of a predetermined size;
    mixing the screened particles with a lubricant;
    loading the particle-lubricant mixture into a mold;

compacting the particle-lubricant mixture in the mold at a predetermined compaction pressure to cause the arm-like projections on the particles to engage and interlock with one another and, form a self-supporting green filter article having a porous, axially-extending outer peripheral wall;

heating the green filter article at a predetermined temperature to burn off the lubricant;

sintering the filter to form a sintered, porous metal filter; and inserting the filter into the interior peripheral wall of an at least partially plastic peripheral member having an axially-extending interior peripheral wall so that at least a continuous peripheral portion of said interior peripheral wall is in contact with said axially-extending outer peripheral surface of said filter; and heating said filter to a temperature sufficient to cause at least a portion of the interior peripheral wall of said peripheral member to flow into the pores of said filter.

18. The product of the process of claim 17.

19. A process of making a filter device for medical injection and infusion equipment and the like, said filter of said filter device being manufactured from metal particles having an irregular or dendritic shape with arm-like projections extending outwardly therefrom; said process comprising the steps of:

compacting the metal particles in a mold in the substantial absence of a binder to cause the arm-like projections on adjacent particles to interlock with one another and form a self-supporting, porous, green article; and sintering said green article to produce a sintered, porous metal filter;

inserting the filter into the interior peripheral wall of an at least partially plastic peripheral member, and heating said filter to a temperature sufficient to cause at least a portion of the interior peripheral wall of said peripheral member to flow into the pores of said filter.

20. The product of the process of claim 19.

21. A process for manufacturing a filter device for medical injection and infusion equipment and the like, said filter of said filter device being manufactured from metal particles having an irregular or dendritic shape with arm-like projections extending outwardly therefrom; said process comprising the steps of:

screening the metal particles to obtain particles of a predetermined size;

mixing the screened particles with a lubricant;

loading the particle-lubricant mixture into a mold;

compacting the particle-lubricant mixture in the mold at a predetermined compaction pressure to cause the arm-like projections on the particles to engage and interlock with one another and form a selfsupporting green article;

heating the green filter article at a predetermined temperature to burn off the lubricant;

sintering the filter article to form a sintered, porous metal filter;

force-fitting said filter into a plastic annular projection within the interior peripheral wall of a tubular member; and heating said filter to a temperature sufficient to cause a peripheral portion of the interior peripheral wall of said plastic annulus to soften and flow into pores in such filter to form a continuous peripheral seal between said tubular member and said filter.

22. The product of the process of claim 21.

* * * * *